(12) United States Patent
Mizunuma et al.

(10) Patent No.: US 12,209,998 B2
(45) Date of Patent: Jan. 28, 2025

(54) PARAMETER DETERMINING DEVICE, PARAMETER DETERMINING METHOD, AND PARAMETER DETERMINING PROGRAM

(71) Applicant: Nippon Telegraph and Telephone Corporation, Tokyo (JP)

(72) Inventors: Mamoru Mizunuma, Musashino (JP); Shingo Mineta, Musashino (JP); Shota Oki, Musashino (JP); Yasuhiro Higashi, Musashino (JP); Soichi Oka, Musashino (JP); Kenichi Tanigaki, Musashino (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 423 days.

(21) Appl. No.: 17/615,753

(22) PCT Filed: May 21, 2020

(86) PCT No.: PCT/JP2020/020036
§ 371 (c)(1),
(2) Date: Dec. 1, 2021

(87) PCT Pub. No.: WO2020/246247
PCT Pub. Date: Dec. 10, 2020

(65) Prior Publication Data
US 2022/0341827 A1 Oct. 27, 2022

(30) Foreign Application Priority Data
Jun. 4, 2019 (JP) .................. 2019-104471

(51) Int. Cl.
*G01N 33/24* (2006.01)
*G01N 3/08* (2006.01)

(52) U.S. Cl.
CPC ............... *G01N 3/08* (2013.01); *G01N 33/24* (2013.01); *G01N 2203/0019* (2013.01); *G01N 2203/0058* (2013.01)

(58) Field of Classification Search
CPC .. G01N 3/08; G01N 33/24; G01N 2203/0019; G01N 2203/0058; G01N 2203/0256; G01N 3/10; E02D 1/02
(Continued)

(56) References Cited

FOREIGN PATENT DOCUMENTS

| CN | 106885891 A | * | 6/2017 |
| WO | WO-2019176836 A1 | * | 9/2019 |

OTHER PUBLICATIONS

Shingo Mineta et al., *Efforts to Estimate the Risk of Communication Equipment Based on the Deterioration Mechanism*, NTT Technology Journal, vol. 29, No. 11, 2017, pp. 19-23.
(Continued)

*Primary Examiner* — Robert R Raevis
(74) *Attorney, Agent, or Firm* — Workman Nydegger (57) ABSTRACT

A soil parameter required when civil engineering/mechanical simulations for various grounds are performed is appropriately determined. A parameter determination device determines a parameter of a particle model used in a ground analysis system. The parameter determination device includes a triaxial compression test numerical analysis unit configured to determine the parameter so that the adhesive force and the shear resistance angle of a virtual ground respectively match the adhesive force and the shear resistance angle of an actual ground with a predetermined accuracy, and a pull-out test numerical analysis unit configured to determine the parameter so that a ground reaction force coefficient of the virtual ground matches a ground reaction force coefficient of the actual ground with a predetermined accuracy.

4 Claims, 6 Drawing Sheets

(58) Field of Classification Search
USPC ........ 73/32 R, 783, 784, 790, 813, 818–822,
73/825, 841, 845, 865.5, 866
See application file for complete search history.

(56) References Cited

OTHER PUBLICATIONS

Shingo Mineta et al., *Consideration on the Corrosion Tendency of the Lower Branch Anchor and the Results of the Outdoor Soil Monitoring Test*, Rust prevention Management (technical report), vol. 61, No. 4, 2017, pp. 137-142.

Japanese Geotechnical Society, *How to Use N Value and $c \times \varphi$*,, Maruzen Publishing Co. Ltd., Apr. 16, 2001, pp. 110-112.

Nils Karajan et al., *On the Parameter Estimation for the Discrete-Element Method in LS-DYNA*, 13th International LS-DYNA Users Conference 2014, Jun. 8, 2014, pp. 1-1-1-9.

Nils Karajan et al, *Interaction Possibilities of Bonded and Loose Particles in LS-DYNA*, 9th European LS-DYNA Conference 2013, Jun. 2, 2013, pp. 1-10.

\* cited by examiner

PARAMETER DETERMINING DEVICE, PARAMETER DETERMINING METHOD, AND PARAMETER DETERMINING PROGRAM

TECHNICAL FIELD

The present invention relates to a method of determining a soil parameter required when civil engineering/mechanical simulations for various grounds are performed.

BACKGROUND ART

In the related art, branch lines are provided to share unbalanced loads of utility poles. In addition, an underground structure such as a branch line anchor and a branch line block is used to fix the branch line to the ground to receive branch line tension. Since it has been many years since the underground structure was laid underground, there is concern about decrease in bearing capacity and the like due to deterioration by corrosion and the like (Non Patent Literatures 1 to 3).

Therefore, various investigations have been performed regarding the maintenance, renewal plan, and the like of the underground structure. For example, when the deterioration and bearing capacity of underground structures are examined, civil engineering and mechanical simulations (numerical analysis simulations) are performed on various grounds, based on the fact that direct observation is difficult because the underground structures are buried in the ground.

CITATION LIST

Non Patent Literature

Non Patent Literature 1: Mineta, et al., "Risk Assessment of Outdoor Telecommunication Facilities Based on Deterioration Mechanisms", NTT Technical Journal, Vol. 29, No. 11, November 2017, p. 19-p. 23
Non Patent Literature 2: Mineta, et al., "Consideration on Corrosion Tendency of Lower Branch Line Anchor and Outdoor Soil Monitoring Test Results", Rust prevention management (technical report), Vol. 61, No. 4, April 2017, p. 13'7-p. 142
Non Patent Literature 3: "How to use N value and c$\varphi$", Japanese Geotechnical Society, 1998, Maruzen Publishing Co., Ltd., p. 110-p. 112
Non Patent Literature 4: Nils Karajan, et al., "On the Parameter Estimation for the Discrete-Element Method in LS-DYNA", 13th International LS-DYNA Users Conference (2014), Jun. 8-10, 2014, p. 1-1-p. 1-9
Non Patent Literature 5: Nils Karajan, et al., "Interaction Possibilities of Bonded and Loose Particles in LS-DYNA", 9th European LS-DYNA Conference (2013)

SUMMARY OF THE INVENTION

Technical Problem

In the case where civil engineering/mechanical simulations for various grounds are performed, it is necessary to determine a soil parameter of a target ground as an input condition for a ground analysis system (ground analysis program software) that performs the simulation. However, there is a problem in that it is difficult to set an appropriate value of the soil parameter.

The present invention has been made in view of the above circumstances, and an object of the present invention is to appropriately determine a soil parameter required for performing civil engineering/mechanical simulations on various grounds.

Means for Solving the Problem

In order to solve the above problem, a parameter determination device according to the present invention determines a parameter of a particle model used in a ground analysis system. The parameter determination device includes an input unit configured to input a test result of a triaxial compression test performed using a specimen of an actual ground, and a determination unit configured to calculate an adhesive force and a shear resistance angle of the actual ground from the test result, calculate an adhesive force and a shear resistance angle of a virtual ground from a test result of a triaxial compression test performed using a specimen of the virtual ground in the ground analysis system, and determine the parameter so that the adhesive force and the shear resistance angle of the virtual ground respectively match the adhesive force and the shear resistance angle of the actual ground with a predetermined accuracy.

The parameter determination device further includes an input unit configured to input a test result of a pull-out test in which a structure is pulled out from the actual ground, and a determination unit configured to calculate a ground reaction force coefficient of the actual ground from the test result, calculate a ground reaction force coefficient of the virtual ground from a test result of a pull-out test performed using the specimen of the virtual ground by the ground analysis system, and determine the parameter so that the ground reaction force coefficient of the virtual ground matches the ground reaction force coefficient of the actual ground with a predetermined accuracy.

According to another aspect of the present invention, there is provided a parameter determination method of determining a parameter of a particle model used in a ground analysis system. The parameter determination method includes, by a parameter determination device, inputting a test result of a triaxial compression test performed using a specimen of an actual ground, and calculating an adhesive force and a shear resistance angle of the actual ground from the test result, calculating an adhesive force and a shear resistance angle of a virtual ground from a test result of a triaxial compression test performed using a specimen of the virtual ground by the ground analysis system, and determining the parameter so that the adhesive force and the shear resistance angle of the virtual ground respectively match the adhesive force and the shear resistance angle of the actual ground with a predetermined accuracy.

The parameter determination method further includes a step of inputting a test result of a pull-out test in which a structure is pulled out from the actual ground, and a step of calculating a ground reaction force coefficient of the actual ground from the test result, calculating a ground reaction force coefficient of the virtual ground from a test result of a pull-out test performed using the specimen of the virtual ground in the ground analysis system, and determining the parameter so that the ground reaction force coefficient of the virtual ground matches the ground reaction force coefficient of the actual ground with a predetermined accuracy.

A parameter determination program according to the present invention causes a computer to perform the parameter determination method.

Effects of the Invention

According to the present invention, it is possible to appropriately determine a soil parameter required for performing civil engineering/mechanical simulations for various grounds.

DESCRIPTION OF EMBODIMENTS

Hereinafter, an embodiment of the present invention will be described with reference to the drawings.

Outline of Embodiment

Particle methods for the ground strength have been reported for the influences of various soil parameter on the action of powder bulk made of small spherical particles (Non Patent Literatures 4 and 5). Thus, in the present embodiment, the particle method is used when civil engineering/mechanical simulations (numerical analysis simulations) for various grounds are performed. In the particle method, for example, rigid particles, the interaction between rigid particles, liquid bridges of rigid particle gaps, surface tension of the liquid bridge, friction forces between rigid particles and container walls, and the like are modeled.

Currently, in a predetermined ground analysis system (ground analysis program software), it is possible to perform the civil engineering/mechanical simulations by numerical analysis using the particle method. For example, the ground analysis system can simulate a triaxial compression test on a specimen of a virtual ground and a pull-out test of an underground structure. Further, in the ground analysis system, it is possible to set a soil parameter for a particle model such as rigid particles before the simulation by numerical analysis is performed.

Figure 1:
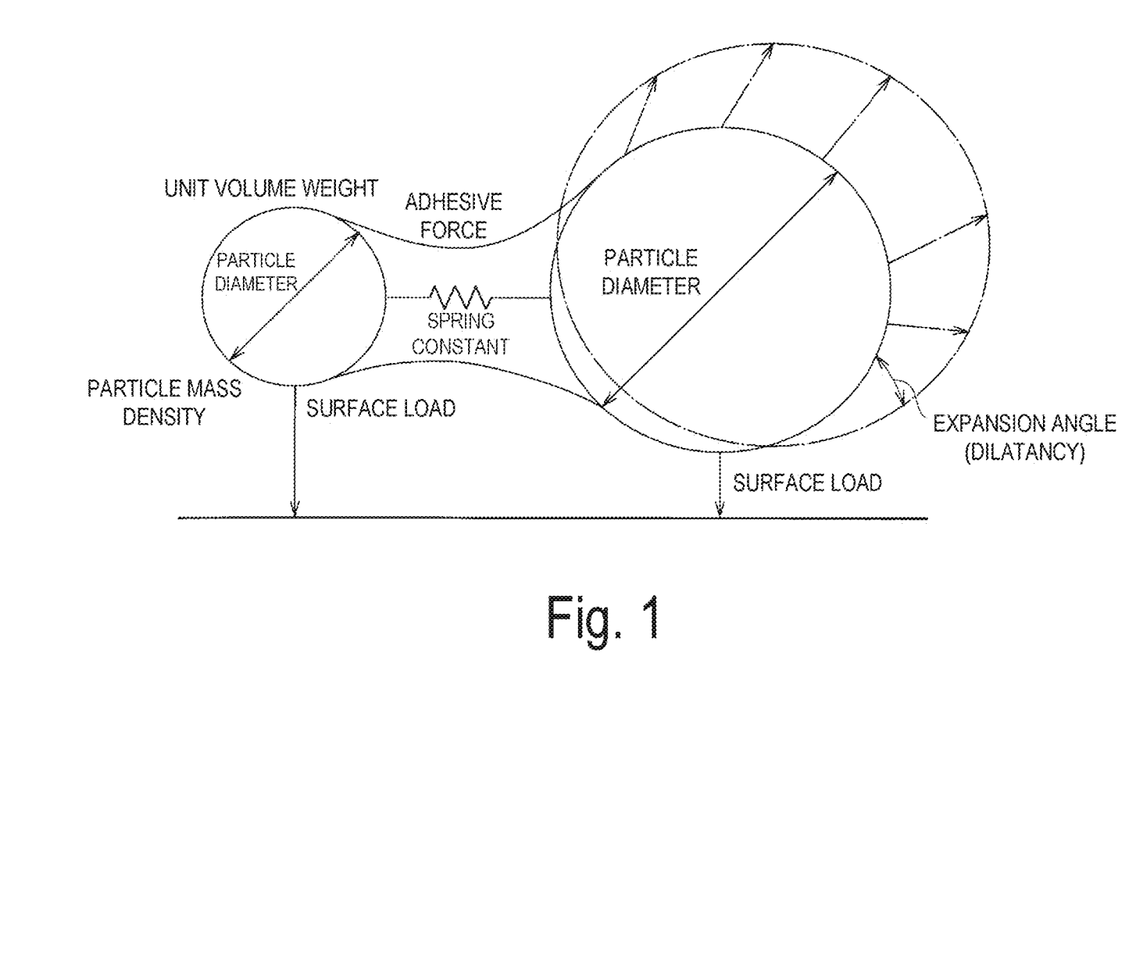
FIG. 1 is a diagram illustrating an example of a soil parameter of a particle model.

FIG. 1 illustrates an example of the soil parameter for a modeled microscopic (micro) particle model. As illustrated in FIG. 1, the soil parameter is, for example, a particle diameter, particle mass density, a surface load, a unit volume weight related to a ground reaction force coefficient, a spring constant, a correction coefficient, an expansion angle (dilatancy), an adhesive force, a shear resistance angle (=internal friction angle), and the like. For details, see Non Patent Literatures 4 and 5.

A user schematically determines the soil parameter of the particle model, sets the parameter in the ground analysis system, and models a cylindrical specimen obtained by virtually simulating a target ground into the ground analysis system to firstly simulate a triaxial compression test.

Figures 2A, 2B:
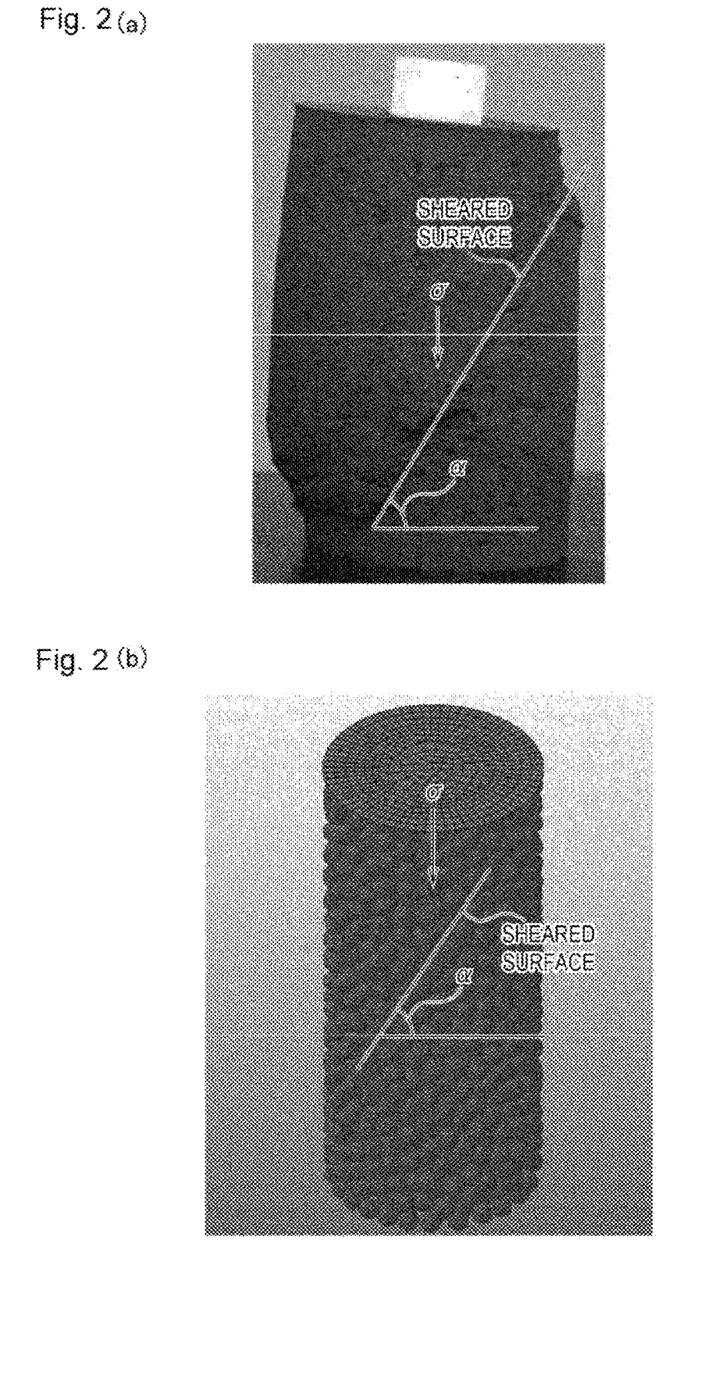
FIG. 2 are views illustrating an example of a sheared surface according to a triaxial compression test.

Generally, in the triaxial compression test, a sheared surface (crack) by shear failure is observed. FIG. 2 are views of the sheared surface observed in the triaxial compression test. FIG. 2(a) illustrates the sheared surface generated in the actual triaxial compression test by a specimen of an actual ground. FIG. 2(b) illustrates a sheared surface generated in the triaxial compression test by a simulation.

The sheared surface angle α can generally be expressed as $\alpha = \pi/4 + \varphi/2$ using a shear resistance angle (=internal friction angle; see FIG. 3) φ. Further, by defining $\tau = c + \sigma \tan \varphi$ using a Mohr-Coulomb ground model illustrated in FIG. 3 as a ground model, it is possible to determine the adhesive force c and the shear resistance angle (=internal friction angle) φ from the sheared surface angle α ($=\pi/4 + \varphi/2$) and the axial stress a during shear failure.

Figure 3:
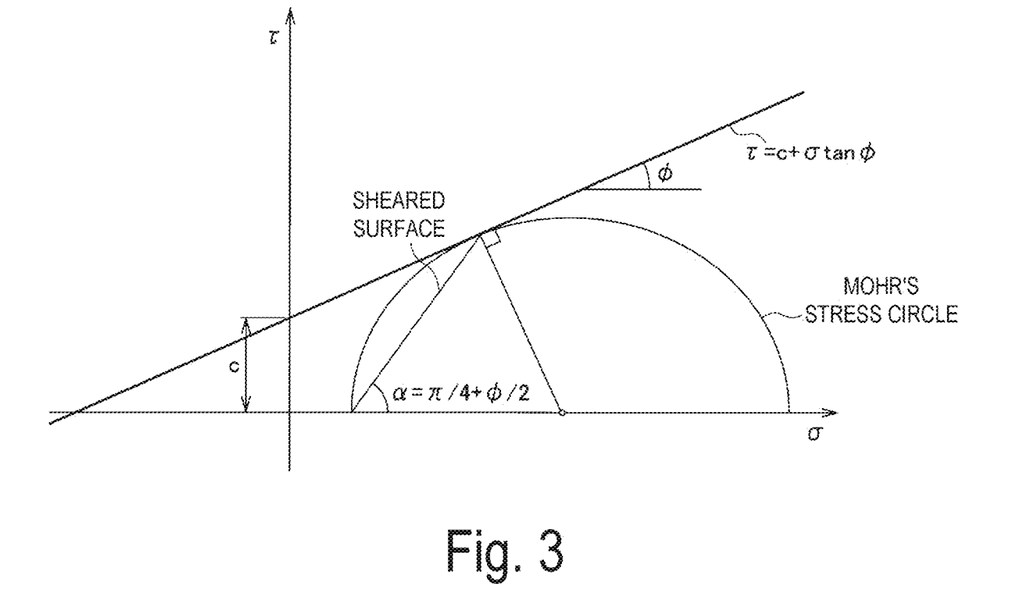
FIG. 3 is a diagram illustrating an example of a Mohr-Coulomb ground model.
Figure 4:
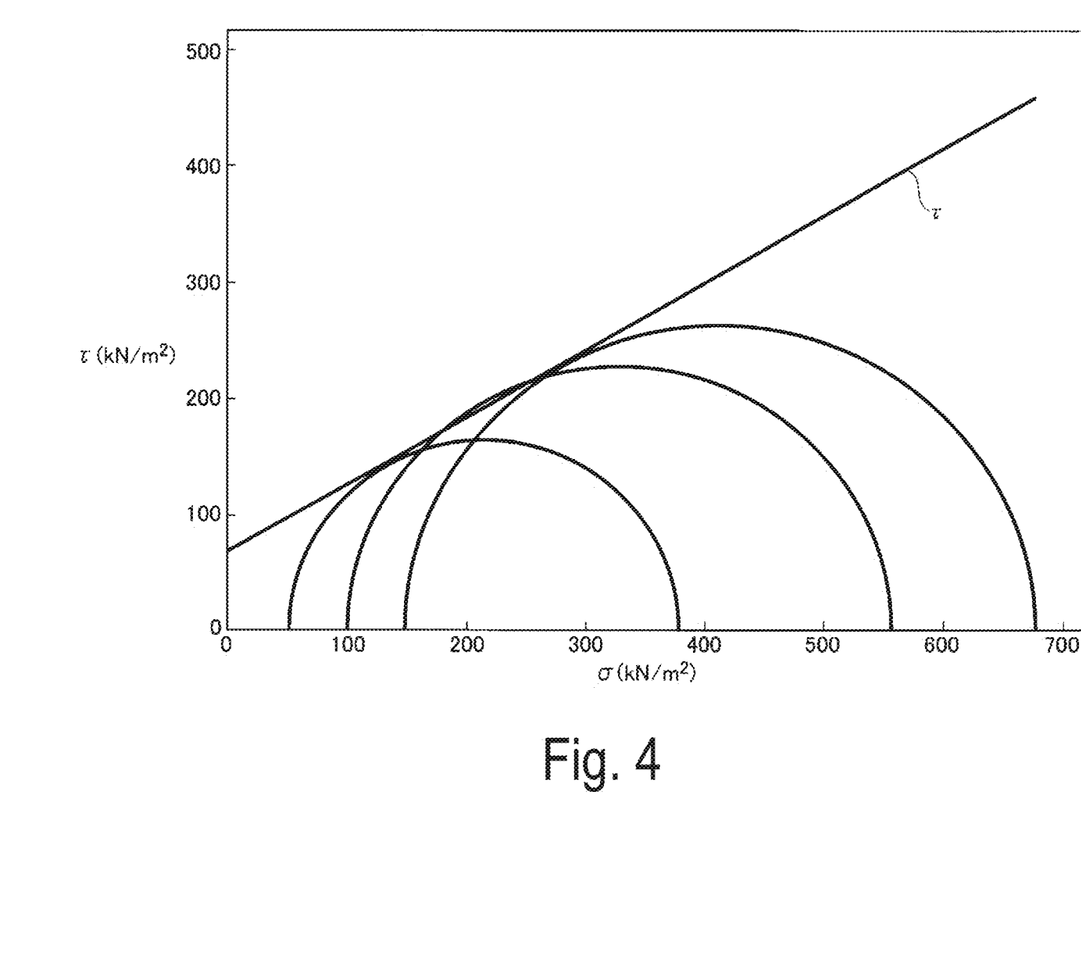
FIG. 4 is a diagram illustrating an example of an output diagram of the triaxial compression tester.

Note that τ ($=c + \sigma \tan \varphi$) indicates shear stress, and is an envelope (fracture envelope) of a plurality of diagrams (stress circles) output when stress conditions are changed using a triaxial compression tester as illustrated in FIG. 4. c and φ are constants for determining fracture conditions and ground strength. In particular, φ has a special significance that φ is a constant for defining the direction of a fracture surface. For basic techniques for α, c, φ, and the like obtained by the triaxial compression test, see "6.2.2 Mohr stress circle and Mohr-Coulomb failure criteria" (p. 110-p. 112) in Non Patent Literature 3.

In the present embodiment, when c1 and φ1 obtained in the actual triaxial compression test using a specimen of a representative test ground and c2 and φ2 obtained by the simulation are matched with desired accuracy, the simulation of a pull-out test of an underground structure in the subsequent stage continues using the set soil parameter. On the other hand, when c1 and φ1 do not match c2 and φ2, reexamination and change of the soil parameter are performed, and thus the simulation of the triaxial compression test is performed again. The soil parameter is adjusted repeatedly until the c2 and φ2 match c1 and φ1 with the above desired accuracy. Then, the adjusted soil parameter is applied to the simulation of the triaxial pressure test performed on the representative test ground.

Then, as the next step, a process for determining the reaction force coefficient of the ground is performed by performing a pull-out test on the underground structure. For example, the pull-out test of a branch line anchor is performed, and as a result, the ground reaction force-displacement curve can be obtained on the graph of stress (horizontal axis) and the amount of displacement (vertical axis). Therefore, a ground reaction force coefficient k is determined using the slope of a straight line near the origin of the graph.

In the present embodiment, k1 obtained by the actual pull-out test using the specimen of the representative test ground actually collected and k2 obtained by the simulation are matched, and the soil parameter is repeatedly adjusted until sufficient agreement is found with each other, that is, k2 matches k1 with desired accuracy. Then, the adjusted soil parameter is applied to the simulation of the pull-out test of the underground structure, which is performed on the representative test ground.

Then, the user performs the civil engineering/mechanical simulation on the representative test ground by using the soil parameter of the particle model, which is adjusted in the two stages.

Configuration of Parameter Determination Device

In the present embodiment, a parameter determination device is used to determine the soil parameter of the particle model used in the ground analysis system. The parameter determination device may operate in the ground analysis system that performs the civil engineering/mechanical simulation, or may operate in a device that is communicably connected to the ground analysis system.

Figure 5:
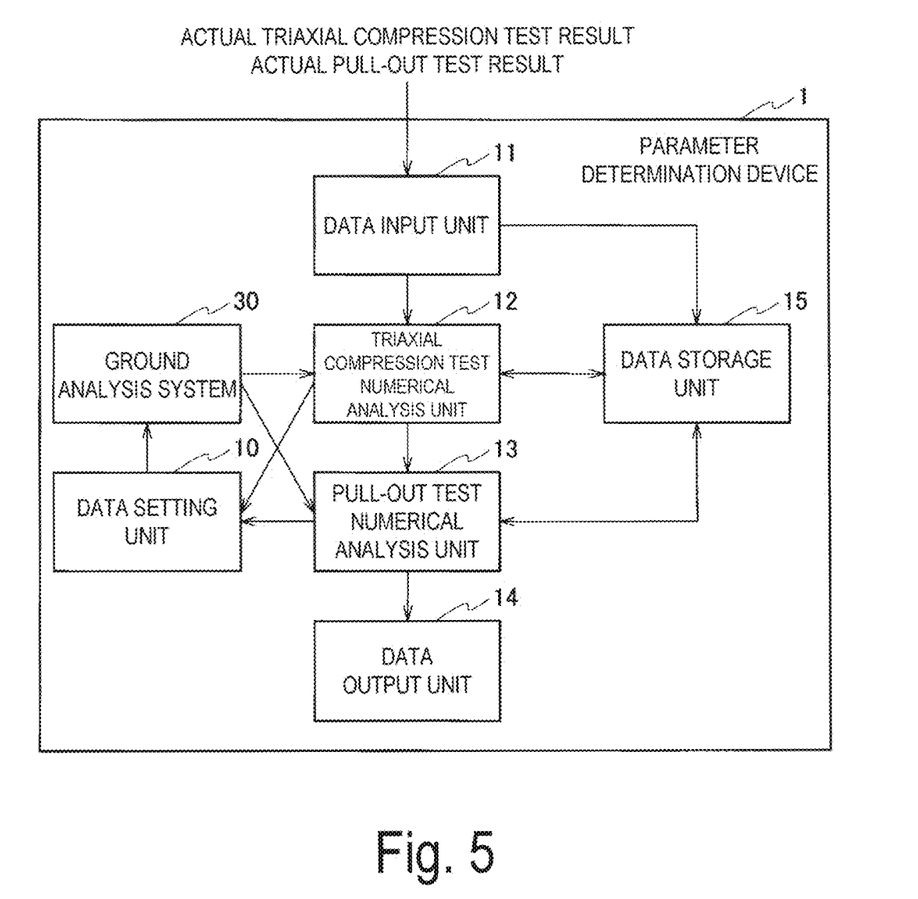
FIG. 5 is a diagram illustrating a configuration example of a functional block of a parameter determination device.

FIG. 5 is a diagram illustrating a configuration example of a functional block of the parameter determination device 1 according to the present embodiment. The parameter determination device 1 mainly includes a data setting unit 10, a data input unit 11, a triaxial compression test numerical analysis unit 12, a pull-out test numerical analysis unit 13, a data output unit 14, and a data storage unit 15.

The data setting unit 10 has a function of setting the configuration of the particle model used in a ground analysis system 30, to the ground analysis system 30. In addition, the data setting unit 10 has a function of setting an initial value of the soil parameter of the particle model determined by the user or the changed value of the soil parameter determined by the triaxial compression test numerical analysis unit 12 or the pull-out test numerical analysis unit 13, in the ground analysis system 30.

The data input unit 11 has a function (input unit) of inputting test result data of an actual triaxial compression test performed using a specimen of an actual ground. In addition, the data input unit 11 has a function (input unit) of inputting test result data of an actual pull-out test in which the underground structure has been pulled out from the actual ground.

The triaxial compression test numerical analysis unit 12 calculates an adhesive force c1 and a shear resistance angle (=internal friction angle) φ1 of the actual ground from the test result data of the triaxial compression test, and calculates an adhesive force c2 and a shear resistance angle (=internal friction angle) φ2 of the virtual ground from the test result data of the triaxial compression test performed in the ground analysis system 30 using the virtual ground test specimen. Then, the triaxial compression test numerical analysis unit 12 has a function (determination unit) of determining the soil parameter of the particle model so that the adhesive force c2 and the shear resistance angle φ2 of the virtual ground match the adhesive force c1 and the shear resistance angle φ1 of the actual ground with a predetermined accuracy.

The pull-out test numerical analysis unit 13 calculates a ground reaction force coefficient k1 of the actual ground from the test result data of the actual pull-out test, and calculates a ground reaction force coefficient k2 of the virtual ground from the test result data of the pull-out test performed in the ground analysis system 30 using the specimen of the virtual ground. Then, the pull-out test numerical analysis unit 13 has a function (determination unit) of determining the soil parameter of the particle model so that the ground reaction force coefficient k2 of the virtual ground matches the ground reaction force coefficient k1 of the actual ground with a predetermined accuracy.

The data output unit 14 has a function of outputting data processed by the parameter determination device 1 to a monitoring device, a storage device, a printing device, or the like. For example, regarding the adhesive force c1 and the shear resistance angle (=internal friction angle) φ1 of the actual ground, and the adhesive force c2 and the shear resistance angle (=internal friction angle) φ2 of the virtual ground, the ground reaction force coefficient k1 of the actual ground, and the ground reaction force coefficient k2 of the virtual ground, the data output unit 14 outputs a comparison result between c1 and c2, a comparison result between φ1 and φ2, a comparison result between k1 and k2, and the like.

The data storage unit 15 has a function of storing data processed by the parameter determination device 1. For example, the data storage unit 15 stores test result data of the actual triaxial compression test, test result data of the actual pull-out test, and the like.

The above-described parameter determination device 1 can be realized by a computer including a CPU, a memory, an input/output interface, a communication interface, and the like, and a program (parameter determination program). Further, the parameter determination program can be recorded on a recording medium or provided via a communication network.

Operation of Parameter Determination Device

Figure 6:
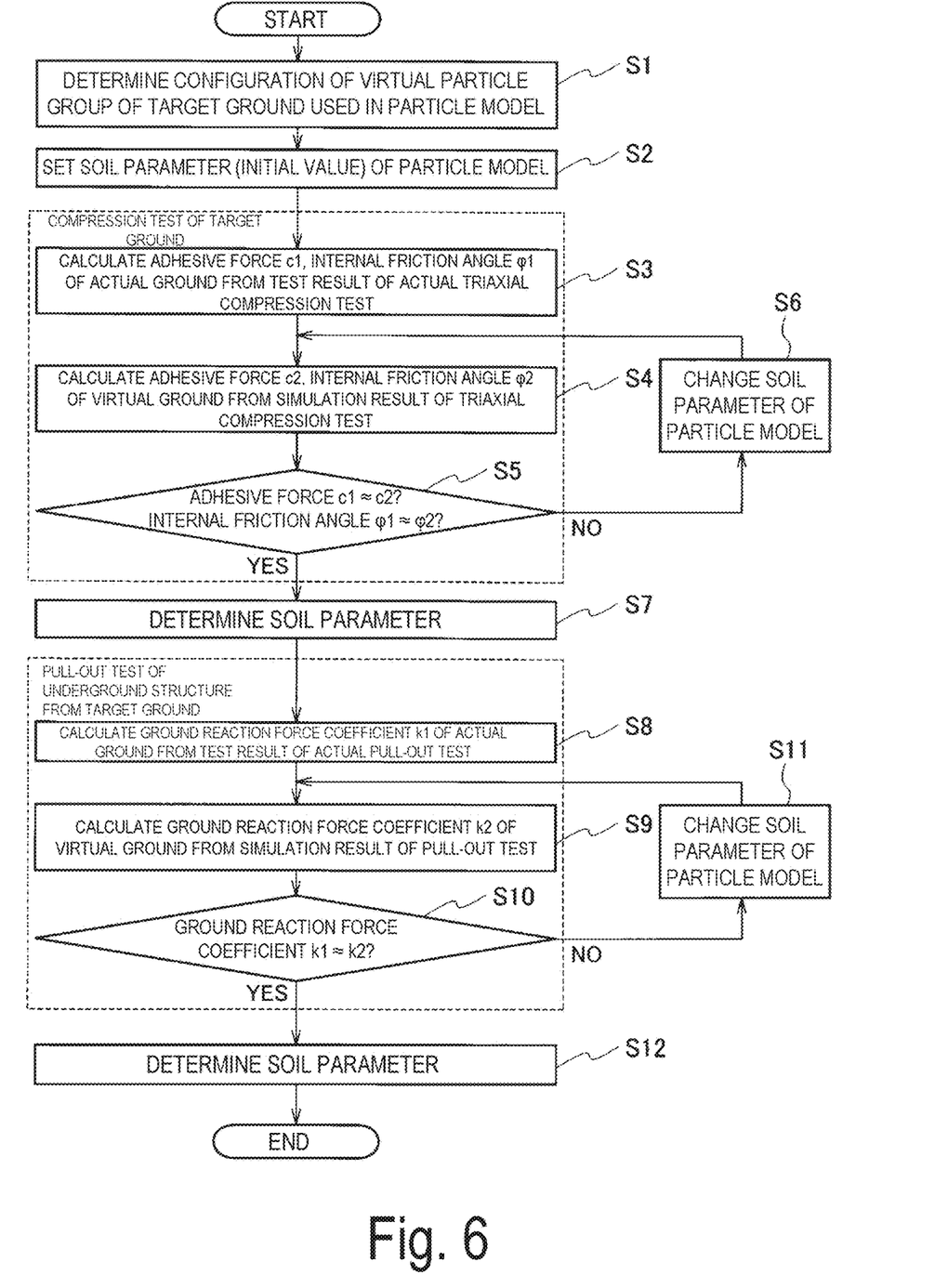
FIG. 6 is a diagram illustrating a parameter determination process flow.

Next, a parameter determination method performed by the parameter determination device 1 will be described. FIG. 6 is a diagram illustrating a parameter determination processing flow according to the present embodiment.

Step S1

Firstly, after the user determines the configuration of the particle model used in the ground analysis system 30, the data setting unit 10 sets the determined configuration of the particle model in the ground analysis system 30. The configuration of the particle model includes, for example, the number of particles, particle coordinates, various coefficients, and the like.

Step S2

Then, the data setting unit 10 has a function of setting the determined initial value of the soil parameter in the ground analysis system 30, after the user determines the initial value of the soil parameter of the particle model. As described above, examples of the soil parameter include a particle diameter, particle mass density, a surface load, a unit volume weight related to a ground reaction force coefficient, a spring constant, a correction coefficient, an expansion angle (dilatancy), an adhesive force, a shear resistance angle (=internal friction angle), and the like.

Steps S3 to S6 (Outline)

Then, firstly, a process of determining the soil parameter of the particle model in the target ground is performed by a triaxial compression test.

For example, in a ground analysis system of which commercial code is "non-linear structure analysis software LS-DYNA", a discrete element method (DEM; particle method) is implemented. Thus, the soil parameter of the particle model described in Non Patent Literature 4 can be set in the ground analysis system. For example, the soil parameter of the target ground can be set by setting the value of the soil parameter in a database associated with the commercial code.

However, it is only possible to roughly estimate what kind of ground model should be adopted as the target ground and what kind of value should be set as the soil parameter of the particle model, and it is difficult to set an appropriate ground model and an appropriate value of the soil parameter. For example, for the ground model, a linear elastic body model, a Mohr-Coulomb ground model, a Drucker—Prager ground model, a Cam-Clay ground model, a Sekiguchi-Ohta ground model, and the like are proposed.

In the present embodiment, among a plurality of ground models, a Mohr-Coulomb ground model ($\tau = c + \sigma \tan \varphi$) having an adhesive force c and a shear resistance angle (=internal friction angle) φ as variables is used. Then, by using the Mohr-Coulomb ground model, it is considered to acquire the items of soil parameters required for the particle model, and input predetermined values of the soil parameters to the ground analysis system.

In the Mohr-Coulomb ground model, a stress circle obtained by drawing the axial stress (normal stress) σ and the shear stress τ in an xy plane (x; horizontal axis, y; vertical axis) of one point in a stressed object, in a σ-τ plane is referred to as Mohr's stress circle (FIG. 3). When a plurality of triaxial compression tests are performed under different stress conditions to draw Mohr's stress circles, and the envelope of the plurality of stress circles is viewed, the envelope can be considered as a straight line (FIG. 4). At this time, the slope φ of the envelope is referred to as the shear resistance angle (=internal friction angle), and the section c of the τ axis is referred to as the adhesive force.

In steps S3 to S5, the Mohr-Coulomb ground model is used to compare the actual triaxial compression test to the simulation of the triaxial compression test. In the triaxial compression test, a sheared surface (crack) is generated on the surface of the specimen of the ground. Thus, using the Mohr-Coulomb ground model (τ=c+σ tan φ), the soil parameter such as the shear resistance angle (=internal friction angle) φ and the soil adhesive force c (τ axis section) can be determined from the sheared surface angle α and the axial stress a at that time. Then, when c2 and φ2 obtained by the simulation do not match φ1 and c1 obtained by the actual triaxial compression test with a predetermined accuracy, the soil parameter of the particle model is changed.

Step S3

Firstly, the user creates a cylindrical specimen of φ50× 100 mm from a target actual ground to perform the actual triaxial compression test using a predetermined compression tester. Then, the data input unit 11 inputs test result data of the actual triaxial compression test performed using the cylindrical specimen of the actual ground. Then, the triaxial compression test numerical analysis unit 12 calculates the adhesive force c1 and the shear resistance angle (=internal friction angle) φ1 of the actual ground from the test result data. Note that the diagram (line diagram) as illustrated in FIG. 3 can be automatically output depending on the compression tester. Thus, the triaxial compression test numerical analysis unit 12 may read c1 and φ1 from the diagram.

Step S4

Then, the user models the cylindrical specimen of φ50× 100 mm as a virtual ground corresponding to the actual ground and performs a triaxial compression test by numerical analysis, in the ground analysis system 30. Specifically, the numerical analysis is performed by solving a dominant equation having the inter-particle distance, the inter-particle angle, the rotational motion, the angular velocity, the attitude angle, and the like as variables, using the current setting value of the soil parameter. Then, the triaxial compression test numerical analysis unit 12 refers to the test result data to take several points from the analysis results (τ, σ) in which the stress value is changed. Then, the triaxial compression test numerical analysis unit uses the Mohr-Coulomb ground model (τ=c+σ tan φ) to calculate the adhesive force c2 and the shear resistance angle (=internal friction angle) φ2 of the virtual ground.

Step S5

Then, the triaxial compression test numerical analysis unit 12 compares the adhesive force c1 and the shear resistance angle (=internal friction angle) φ1 of the actual ground, which are calculated in step S3, with the adhesive force c2 and the shear resistance angle (=internal friction angle) φ2 of the virtual ground, which are calculated in step S4, and determines whether or not the adhesive force c1 and the shear resistance angle φ1 respectively match the adhesive force c2 and the shear resistance angle φ2 with high accuracy. For example, when a first determination expression of "$c_{MIN} \le c2 \le c_{MAX}, \varphi_{MIN} \le \varphi2 \le \varphi_{MAX}$" is established, the triaxial compression test numerical analysis unit 12 determines that the adhesive forces and the shear resistance angles match with high accuracy. When the first determination expression is not established, the triaxial compression test numerical analysis unit determines that the adhesive forces and the shear resistance angles do not match. Note that $c_{MIN}$ and $c_{MAX}$, and cMAX indicate respectively the minimum value $_cMIN$ and the maximum value $_cMAX$, which are defined in consideration of predetermined required accuracy with respect to the adhesive force c1 obtained in the actual triaxial compression test. The $\varphi_{MIN}$ and $\varphi_{MAX}$ indicate respectively the minimum value $_\varphi MIN$ and the maximum value $_\varphi MAX$, which are defined in consideration of predetermined required accuracy, with respect to the shear resistance angle obtained in the actual triaxial compression test.

Step S6

As a result of the determination performed in step S5, when c2 and φ2 do not match c1 and φ1 with high accuracy, or c2 and φ2 deviate from c1 and φ1, the process returns to the setting process of the soil parameter of the particle model. The triaxial compression test numerical analysis unit 12 examines the soil parameter and modifies or changes the current setting value of the soil parameter. Then, steps S4 and S5 are performed again. The triaxial compression test numerical analysis unit 12 repeats steps S4 to S6 until c2 and φ2 satisfy the first determination expression.

For example, the control term that needs firstly to be examined is a spring constant between virtual particles, and other items are adjusted correction coefficients. For example, when the waist circumference becomes large due to the deformation caused by the simulation of the cylindrical specimen by the triaxial compression test, since the spring constant between the virtual particles is considered to be too small, firstly, the spring constant is changed to a large value, and then the simulation is performed again. After the correction coefficient is adjusted, the Mohr-Coulomb ground model (parameter value) having the sufficiently accurate adhesive force c and shear resistance angle (=internal friction angle) φ is determined.

Step S7

As a result of the determination performed in step S5, when c2 and φ2 match c1 and φ1 with high accuracy, the current setting value of the soil parameter is determined to be the value of the soil parameter of the particle model. Then, the process proceeds to the implementation of the civil engineering/mechanical simulation of an underground structure.

Steps S8 to S11 (Outline)

A process of determining the soil parameter of the particle model in the target ground is performed in a manner that the reaction force coefficient of the target ground is determined by the pull-out test of the branch line anchor performed in the target ground.

When the upper end of the buried lower branch line anchor is pulled upward, the stress σ and the amount of displacement δ occurring in the branch line anchor has a proportional relationship in a range of small displacement δ. The proportion coefficient is generally referred to as the ground reaction force coefficient k (=σ/δ). The ground reaction force-displacement curve in a range beyond the linear range where no apparent fracture is seen in the ground indicates a non-linear relationship.

For example, in the ground analysis system of the commercial code described above, an analysis simulation obtained by simulating the pull-out test of the branch line anchor is performed, and thus it is possible to obtain the ground force-amount of displacement curve on a graph of stress and displacement, and to determine the ground reaction force coefficient k based on the slope of the straight line near the origin of the graph.

Thus, in steps S8 to S11, the ground reaction force coefficients k1 and k2 are obtained by an actual pull-out test and a simulation of the pull-out test. When k2 by the simulation does not match k1 by the actual pull-out test with a predetermined accuracy, the soil parameter of the particle model is changed.

Step S8

Firstly, the user performs the actual pull-out test of the branch line anchor by using the cylindrical specimen of the actual ground. Then, the data input unit 11 inputs test result data of the actual pull-out test performed using the cylindrical specimen of the actual ground. Then, the pull-out test numerical analysis unit 13 calculates the ground reaction force coefficient k1 of the actual ground from the test result data of the actual pull-out test.

Step S9

Then, in the ground analysis system 30, the user performs the triaxial compression test by numerical analysis using the cylindrical specimen of the virtual ground. Specifically, the numerical analysis is performed by solving a dominant equation having the inter-particle distance, the inter-particle angle, the rotational motion, the angular velocity, the attitude angle, and the like as variables, using the current setting value of the soil parameter. Then, the pull-out test numerical analysis unit 13 calculates the ground reaction force coefficient k2 of the virtual ground using the test result data.

Step S10

Then, the pull-out test numerical analysis unit 13 compares the ground reaction force coefficient k1 of the actual ground calculated in step S8 with the ground reaction force coefficient k2 of the virtual ground calculated in step S9 to determine whether k1 and k2 match each other with high accuracy. For example, when a second determination expression of "k1−δp≤k2≤k1+δp" is established, it is determined that k1 and k2 match with high accuracy, and when the second determination expression is not established, it is determined that k1 and k2 do not match each other. Note that (k1−δp) and (k1+δp) are the minimum value and the maximum value in consideration of predetermined required accuracy with respect to the ground reaction force coefficient k1 obtained in the actual pull-out test. δp is a predetermined required error value.

Step S11

As a result of the determination performed in step S10, when k2 does not match k with high accuracy or deviates from k, the process returns to the setting process of the soil parameter of the particle model. The pull-out test numerical analysis unit 13 examines the soil parameter again and modifies or changes the current setting value of the soil parameter. Then, steps S9 and S10 are performed again. The pull-out test numerical analysis unit 13 repeats steps S9 to S11 until k2 satisfy the second determination expression.

For example, the soil parameter such as the unit volume weight $\gamma$, the adhesive force c, the shear resistance angle (=internal friction angle) $\varphi$, and the expansion angle $\psi$ (dilatancy) is adjusted. Because the adhesive force c and the shear resistance angle (=internal friction angle) $\varphi$ have been determined in an examination stage associated with the triaxial compression test, only the minimum term is modified in this stage. For example, the expansion angle $\psi$ (dilatancy) involved in the load being released and increasing in volume from a normal compaction state is not modified because the expansion angle does not vary greatly.

Thus, here for example, the modification is performed with an adjustment method using the unit volume weight $\gamma$ as the center. Specifically, when the ground reaction force coefficient k is small, the unit volume weight $\gamma$ is changed to a small value. When the ground reaction force coefficient is large, the unit volume weight $\gamma$ is changed to a large value.

Step S12

As a result of the determination performed in step S10, when k2 matches k1 with high accuracy, the current setting value of the soil parameter is determined to the value of the soil parameter of the particle model.

Then, the ground analysis system 30 performs the numerical analysis simulation using the particle method regarding the ground strength using the value of the soil parameter of the particle model set in the two stages of steps S7 and S12.

Advantages

Hitherto, according to the present embodiment, the soil parameter of the micro-particle method used for structural evaluation of the underground structure by numerical analysis is determined so that macro ground parameters (c1, $\varphi$1, k1) which can be acquired in two stages of the triaxial compression test and the pull-out test of the underground structure match ground parameters (c2, $\varphi$2, k2) by the simulation, with the desired accuracy. Therefore, according to the present embodiment, it is possible to appropriately determine the soil parameter required when civil engineering/mechanical simulations for various grounds are performed, and to perform highly numerical analysis (simulation).

In the particle method, the microscopic (micro) soil parameter is used to model the powder bulk. When the simulation is performed using the particle method with a common ground analysis system, numerical analysis is to be performed based on the micro model. The analysis according to the micro model does not guarantee computational accuracy for the civil engineering and mechanical analysis of underground structures. However, as described above, when the result of the macro triaxial compression test showing that the parameter of the practical Mohr-Coulomb ground model precisely matches the result of the actual compression test is obtained, it is considered that the numerical analysis can be performed. That is, it is possible to ensure that the numerical analysis is performed by a model in which the soil parameter of the particle method supported by the macro parameters c and $\varphi$ are set.

When the micro model according to the particle method and the macro model using the Mohr-Coulomb ground model are deviated, it is possible to realize that modification of the soil parameter is necessary before the numerical analysis implementation requiring a large amount of time, and waste on the numerical analysis can be eliminated.

Further, there is a high possibility that the micro model of the particle method can be more accurate.

REFERENCE SIGNS LIST

1 Parameter determination device
10 Data setting unit
11 Data input unit
12 Triaxial compression test numerical analysis unit
13 Pull-out test numerical analysis unit
14 Data output unit
15 Data storage unit

The invention claimed is:

1. A parameter determination device that determines a parameter of a particle model used in a ground analysis system, the parameter determination device comprising:
a data input unit configured to input a test result of a triaxial compression test performed using a specimen of an actual ground; and
a determination unit configured to:
calculate an adhesive force and a shear resistance angle of the actual ground from the test result,
calculate an adhesive force and a shear resistance angle of a virtual ground from a test result of a triaxial compression test performed using a specimen of the virtual ground in the ground analysis system, and
determine the parameter after the adhesive force and the shear resistance angle of the virtual ground respectively match the adhesive force and the shear resistance angle of the actual ground with a predetermined accuracy, wherein a simulation is performed using the determined parameter.

2. The parameter determination device according to claim 1, wherein:
the data input unit is configured to input a test result of a pull-out test in which a structure is pulled out from the actual ground; and
the determination unit is configured to:
calculate a ground reaction force coefficient of the actual ground from the test result,
calculate a ground reaction force coefficient of the virtual ground from a test result of a pull-out test performed using the specimen of the virtual ground in the ground analysis system, and
determine the parameter after the ground reaction force coefficient of the virtual ground matches the ground reaction force coefficient of the actual ground with a predetermined accuracy.

3. A parameter determination method of determining a parameter of a particle model used in a ground analysis system, the parameter determination method comprising:
performing, by a parameter determination device:
inputting a test result of a triaxial compression test performed using a specimen of an actual ground; and
calculating an adhesive force and a shear resistance angle of the actual ground from the test result, calculating an adhesive force and a shear resistance angle of a virtual ground from the test result of the triaxial compression test performed using a specimen of the virtual ground in the ground analysis system, and determining the parameter after the adhesive force and the shear resistance angle of the virtual ground respectively match the adhesive force and the shear resistance angle of the actual ground with a predetermined accuracy; and
performing a simulation using the determined parameter.

4. The parameter determination method according to claim 3, the parameter determination method further comprising:
inputting a test result of a pull-out test in which a structure is pulled out from the actual ground; and
calculating a ground reaction force coefficient of the actual ground from the test result, calculating a ground reaction force coefficient of the virtual ground from a test result of a pull-out test performed using the specimen of the virtual ground in the ground analysis system, and determining the parameter after the ground reaction force coefficient of the virtual ground matches the ground reaction force coefficient of the actual ground with a predetermined accuracy.

* * * * *